(12) United States Patent
Shelton, IV

(10) Patent No.: US 12,310,587 B2
(45) Date of Patent: May 27, 2025

(54) COMPOSITE INTERCONNECTED ANVIL FOR MEDICAL STAPLER

(71) Applicant: CILAG GMBH INTERNATIONAL, Zug (CH)

(72) Inventor: Frederick E. Shelton, IV, Hillsboro, OH (US)

(73) Assignee: CILAG GMBH INTERNATIONAL, Zug (CH)

( * ) Notice: Subject to any disclaimer, the term of this patent is extended or adjusted under 35 U.S.C. 154(b) by 0 days.

(21) Appl. No.: 18/503,731

(22) Filed: Nov. 7, 2023

(65) Prior Publication Data
US 2025/0143700 A1 May 8, 2025

(51) Int. Cl.
*A61B 17/072* (2006.01)

(52) U.S. Cl.
CPC ............ *A61B 17/07207* (2013.01); *A61B 2017/07264* (2013.01); *A61B 2017/07285* (2013.01)

(58) Field of Classification Search
CPC ................................................ A61B 17/0727
See application file for complete search history.

(56) References Cited

U.S. PATENT DOCUMENTS

| | | | |
|---|---|---|---|
| 7,866,525 B2 | 1/2011 | Scirica | |
| 8,875,972 B2 * | 11/2014 | Weisenburgh, II | A61B 17/105 227/176.1 |
| 9,833,241 B2 | 12/2017 | Huitema | |
| 9,844,369 B2 | 12/2017 | Huitema | |
| 9,877,721 B2 | 1/2018 | Schellin | |
| 10,010,324 B2 | 7/2018 | Huitema | |
| 10,835,250 B2 * | 11/2020 | Weisenburgh, II | A61B 17/105 |
| 11,179,155 B2 * | 11/2021 | Shelton, IV | A61B 17/068 |
| 2009/0206137 A1 * | 8/2009 | Hall | A61B 17/07207 227/176.1 |
| 2009/0206138 A1 * | 8/2009 | Smith | A61B 17/07207 227/176.1 |
| 2009/0206140 A1 * | 8/2009 | Scheib | A61B 17/07207 227/176.1 |
| 2015/0297228 A1 | 10/2015 | Huitema | |
| 2017/0281186 A1 | 10/2017 | Shelton, IV | |
| 2017/0367695 A1 | 12/2017 | Shelton, IV | |
| 2018/0168575 A1 | 6/2018 | Simms | |
| 2018/0368839 A1 * | 12/2018 | Shelton, IV | A61B 17/07207 |
| 2019/0015099 A1 | 1/2019 | Cappola | |
| 2020/0289112 A1 | 9/2020 | Whitfield et al. | |

* cited by examiner

*Primary Examiner* — Nathaniel C Chukwurah
(74) *Attorney, Agent, or Firm* — TROUTMAN PEPPER LOCKE LLP

(57) ABSTRACT

A medical stapler anvil including an anvil pocket beam and an anvil back beam. The anvil pocket beam can include a plurality of staple forming pockets and an anvil pocket beam moment of inertia. The anvil back beam can be fixedly attached to the anvil pocket beam and can include a crown disposed opposite the plurality of staple forming pockets and an anvil back beam moment of inertia approximately equal to the anvil pocket beam moment of inertia. The anvil pocket beam and the anvil back beam can be stamped from sheet metal.

16 Claims, 12 Drawing Sheets

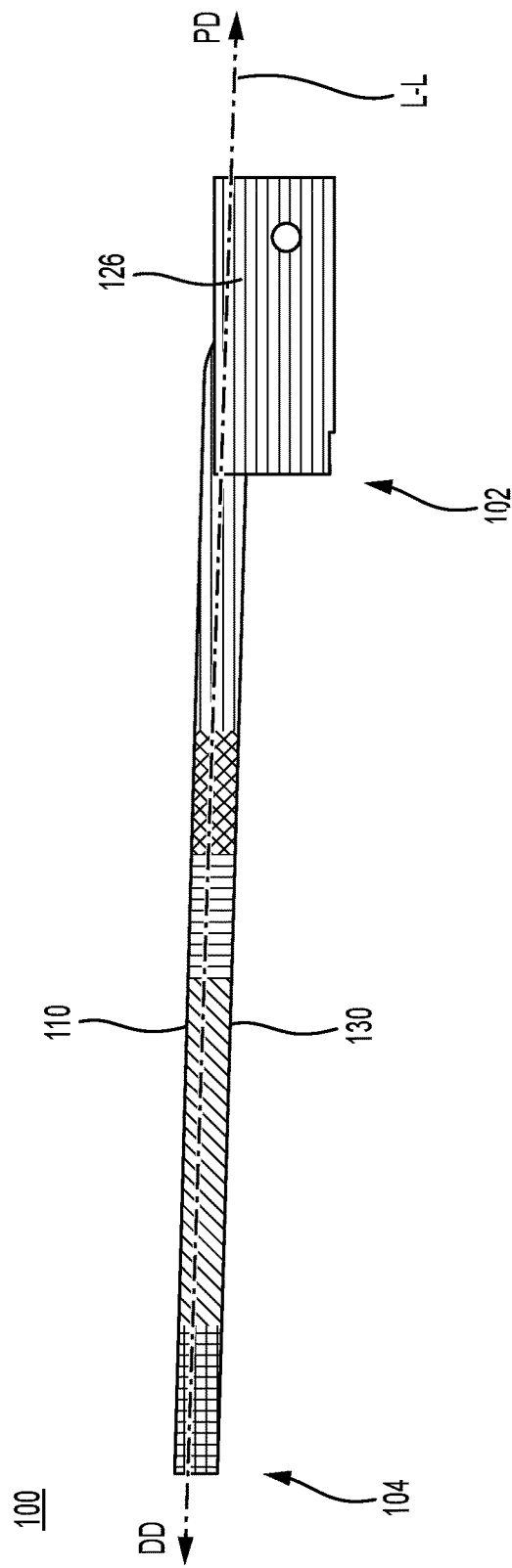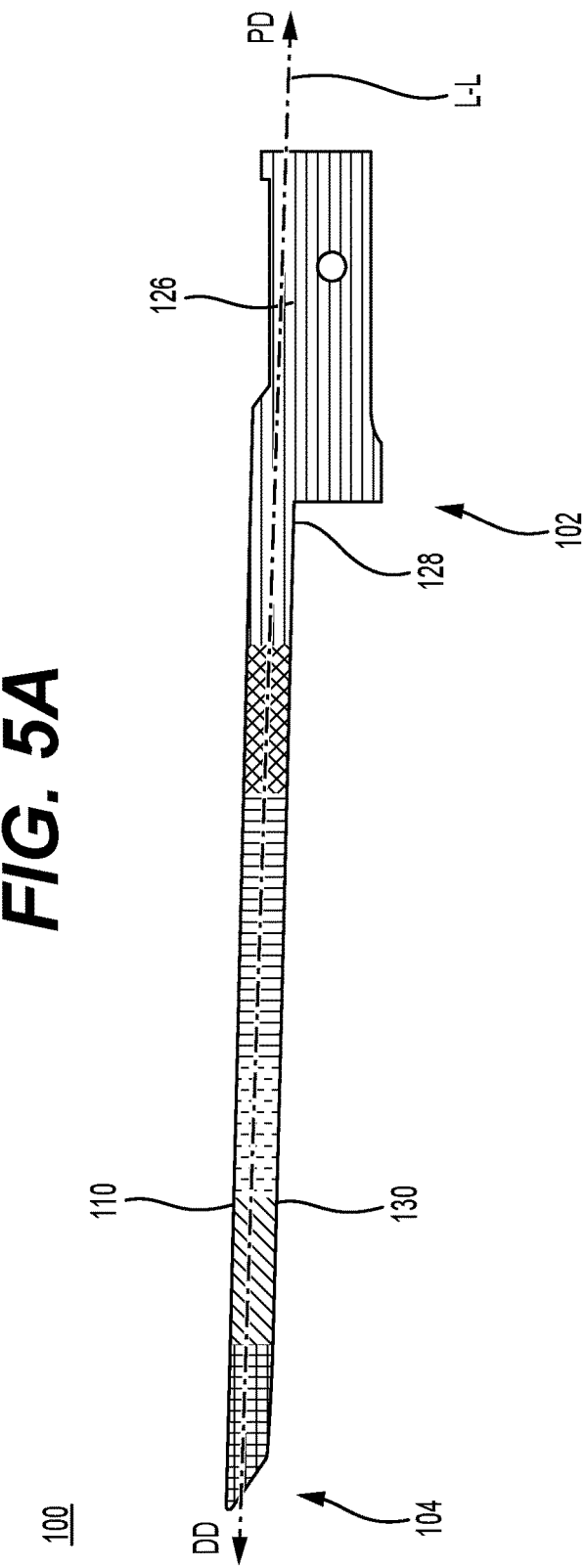

COMPOSITE INTERCONNECTED ANVIL FOR MEDICAL STAPLER

FIELD OF THE INVENTION

The present disclosure relates to surgical instruments and, in various arrangements, to surgical stapling and cutting instruments and end effectors for use therein that are designed to staple and cut tissue.

BACKGROUND

Stapling and cutting of tissue are both affected by the clamping pressure applied to tissue by the medical stapler jaws. Staples are designed to be driven through a certain thickness of tissue. If insufficient or uneven clamping pressure is applied at any point along the length of the medical stapler jaws, some or all of the staples may not curl which can result in inadequate hemostasis, among other problems. The nature of staple jaws poses this problem—staple jaws can be approximated as beams, and deflection of the beam under a load increases along a beam's length. To reduce this deflection and its negative effects on the stapling and cutting for which the medical stapler is employed, the medical stapler jaws must be sufficiently rigid.

Medical stapler jaws which are sufficiently rigid to suit their purpose are expensive and labor intensive to manufacture. Most typically they are machined from medical-grade metal. With the market for medical staplers being in the billions of dollars, significant economic benefit can be gained from making them more cheaply while maintaining strength. Additionally, machining is noted to create more waste than some other methods of manufacturing metal parts. However, machined medical stapler anvils remain a disproportionate source of manufacturing complexity and cost in the production of medical staplers.

Thus, there is a need for a sufficiently rigid medical stapler anvil that can be produced more cheaply and with less waste.

SUMMARY

It is an object of the present disclosure to provide devices and methods to meet the above-stated needs. The systems, devices, and methods relate to staplers used in minimally invasive surgeries.

The instant disclosure describes a medical stapler anvil. The medical stapler can include an anvil pocket beam and an anvil back beam. The anvil pocket beam can include a plurality of staple forming pockets and an anvil pocket beam moment of inertia. The anvil back beam can be fixedly attached to the anvil pocket beam and can include a crown disposed opposite the plurality of staple forming pockets and an anvil back beam moment of inertia approximately equal to the anvil pocket beam moment of inertia.

The instant disclosure describes an anvil for a medical stapler, the anvil extending along a longitudinal axis from a proximal end to a distal end and can include a first section and a second section. The first section can include a shaped sheet including a central ridge parallel to the longitudinal axis, a first lateral side, and a second lateral side. The first side can extend from the central ridge and can include a first inferior ridge, a first trough disposed between the first inferior ridge and the central ridge, a first outer edge, and a first curled end. The second lateral side can extend from the central ridge and can include a second inferior ridge, a second trough disposed between the second inferior ridge and the central ridge, a second outer edge, and a second curled end. The second section can include a pocket surface in contact with the first and second curled ends, a first folded edge disposed proximate the first outer edge, and a second folded edge disposed proximate the second outer edge.

The instant disclosure describes a method of forming an anvil for use in a medical stapler. The method can include stamping a central ridge into a first metal sheet, curling ends of the first metal sheet to form outer edges having curled ends, folding a second metal sheet to form two upfolded edges, stamping a plurality of staple forming pockets into the second metal sheet, placing a pocket surface of the second metal sheet and the two upfolded edges in contact with the curled ends, and welding the first metal sheet to the second metal sheet where the upfolded edges contact the outer edges.

BRIEF DESCRIPTION OF THE DRAWINGS

FIG. 5A shows a side view of a medical stapler anvil, according to aspects of the present disclosure.

FIG. 5B shows a side view of a medical stapler anvil, according to aspects of the present disclosure.

DETAILED DESCRIPTION

Figure 1:
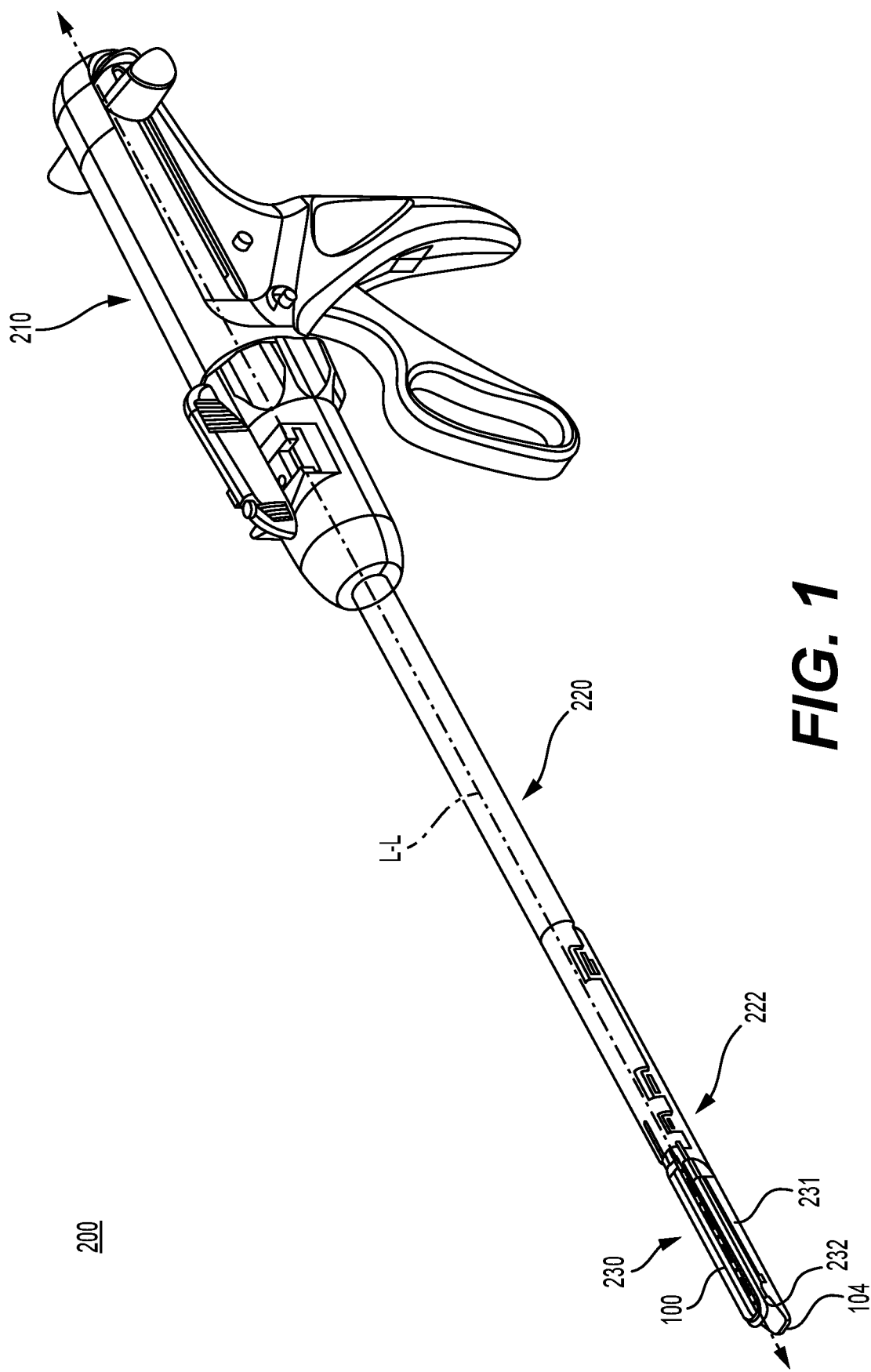
FIG. 1 shows a medical stapler, according to aspects of the present disclosure.

The disclosed technology relates to improving or maintaining the performance of medical staplers, particularly their anvils, while reducing manufacturing cost, complexity, and associated waste. A stamped sheet metal anvil, such as that described in various examples herein, achieves this in part by virtue of the simplicity, reduced cost, and inherent reduction of waste associated with sheet metal stamping processes.

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

Numerous specific details are set forth to provide a thorough understanding of the overall structure, function, manufacture, and use of the embodiments as described in the specification and illustrated in the accompanying drawings. Well-known operations, components, and elements have not been described in detail so as not to obscure the embodiments described in the specification. The reader will understand that the embodiments described and illustrated herein are non-limiting examples, and thus it can be appreciated that the specific structural and functional details disclosed herein may be representative and illustrative. Variations and changes thereto may be made without departing from the scope of the claims.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a surgical system, device, or apparatus that "comprises," "has," "includes" or "contains" one or more elements possesses those one or more elements but is not limited to possessing only those one or more elements. Likewise, an element of a system, device, or apparatus that "comprises," "has," "includes" or "contains" one or more features possesses those one or more features but is not limited to possessing only those one or more features.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g. "about 90%" may refer to the range of values from 71% to 110%. In addition, as used herein, the terms "patient," "host," "user," and "subject" refer to any human or animal subject and are not intended to limit the systems or methods to human use, although use of the subject invention in a human patient represents a preferred example. It should be appreciated that an animal can be a variety of any applicable type, including, but not limited thereto, mammal, veterinarian animal, livestock animal or pet type animal, etc. As an example, the animal can be a laboratory animal specifically selected to have certain characteristics similar to a human (e.g., rat, dog, pig, monkey, or the like). It should be appreciated that the subject can be any applicable human patient, for example. As well, the term "proximal" indicates a location closer to the operator or physician whereas "distal" indicates a location further away to the operator or physician.

As discussed herein, "physician" can include a doctor, surgeon, technician, scientist, operator or any other individual or delivery instrumentation associated with minimally invasive medical operations on a subject.

Furthermore, the use of "couple", "coupled", "attach", "attached", or similar phrases should not be construed as being limited to a certain number of components or a particular order of components unless the context clearly dictates otherwise.

Various exemplary devices and methods are provided for performing laparoscopic and minimally invasive surgical procedures. However, the reader will readily appreciate that the various methods and devices disclosed herein can be used in numerous surgical procedures and applications including, for example, in connection with open surgical procedures. As the present Detailed Description proceeds, the reader will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and an elongate shaft of a surgical instrument can be advanced.

A medical stapler 200 is illustrated in FIG. 1. The medical stapler 200 is configured to grasp, clamp, incise, and seal patient tissue and has a staple cartridge 232. The medical stapler 200 can include a handle assembly 210 that has an elongated shaft 220 protruding therefrom to an end effector 230.

The end effector 230 comprises a first jaw 231 with a staple cartridge 232 and a second jaw/anvil 100. The second jaw/anvil 100 is configured to deform staples ejected from the staple cartridge 232. The distal end 104 of the anvil is disposed furthest from the handle assembly 210. The anvil 100 is pivotable relative to the first jaw 231; however, other embodiments are envisioned in which the first jaw 231 is pivotable relative to the anvil 100. The medical stapler 200 can in some examples include an articulation joint 222 configured to permit the end effector 230 to be rotated, or articulated, relative to the shaft 220. Other embodiments are envisioned which do not include an articulation joint. In other words, other elements described herein can be employed in embodiments where no articulation joint is provided without departing from the spirit and scope of the present disclosure. Similarly, the articulation joint 222 can be employed in embodiments where other elements described herein are omitted.

Figure 2A:
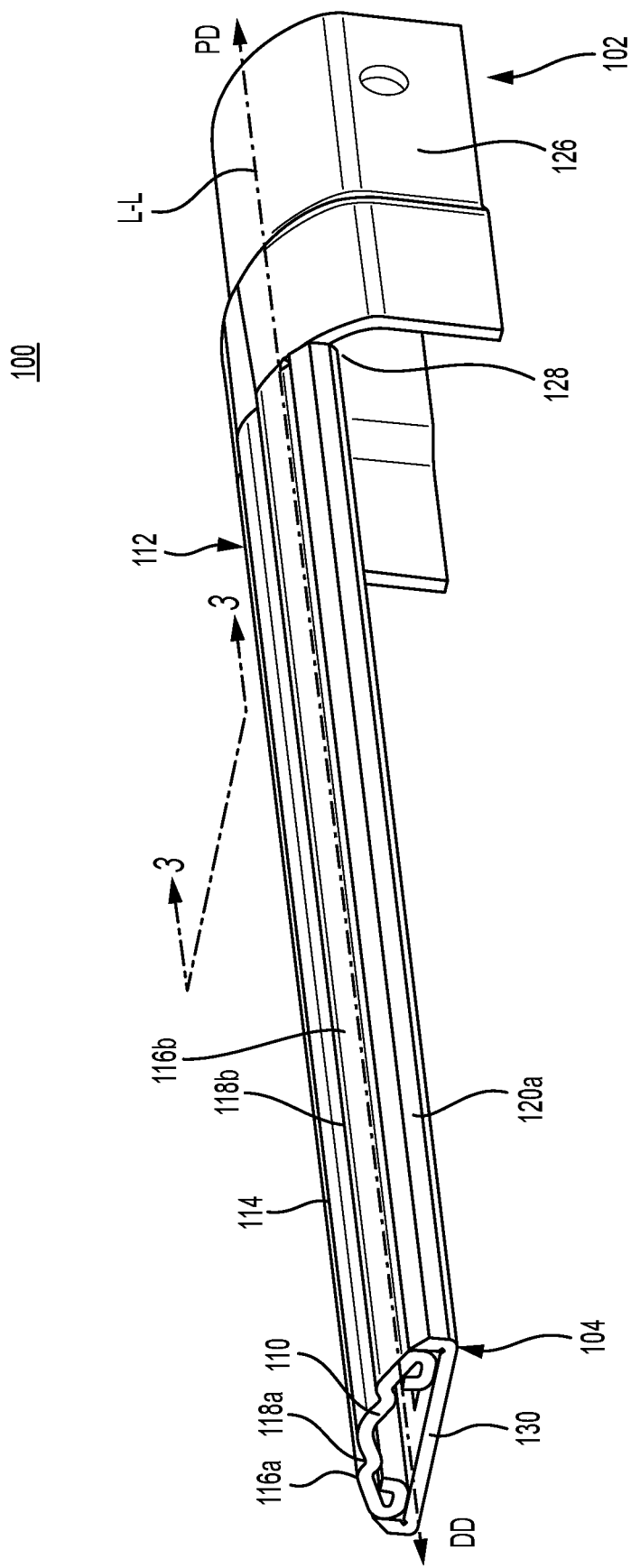
FIG. 2A shows a perspective view of a medical stapler anvil, according to aspects of the present disclosure.

FIG. 2A is a perspective view of a medical stapler anvil 100. The medical stapler anvil 100 includes an anvil pocket beam 130 and an anvil back beam 110. Anvil pocket beam 130 includes a plurality of staple forming pockets 142 (shown in FIGS. 6A-6B and discussed in more detail in relation thereto) and an anvil pocket beam moment of inertia. Anvil back beam 110 can be fixedly attached to the anvil pocket beam 130. Anvil back beam 110 and anvil pocket beam 130 can be attached to one another, for example via welds. As used herein, welding refers generally to the fusing of metals and can include all manners of welding known to those of skill in the art as well as soldering and brazing. Anvil back beam 110 includes a crown 112 disposed opposite the plurality of staple forming pockets 142 of anvil pocket beam 130, that is to say, on the side of the end effector 230 not for clamping the tissue. Anvil back beam 130 includes an anvil back beam moment of inertia. The anvil back beam moment of inertia can in some examples be approximately equal to the anvil pocket beam moment of inertia. Furthermore, the medical stapler anvil 100 can extend from a proximal end 102 to the distal end 104 along a longitudinal axis L-L disposed therebetween.

Anvil 100 can further include a coupling portion 126 disposed proximate the proximal end 102 of the anvil 100. The coupling portion 126 can in some examples serve to create, along with a pin, a hinged union between the anvil 100 and the staple cartridge jaw to allow the pivoting previously mentioned. Coupling portion 126 can also serve to fixedly attach the anvil 100 directly to the shaft 220 (or a respective coupling portion disposed at the shafts proximal end), and in this example the first jaw 231 with the staple cartridge 232 would pivot relative to the longitudinal axis L-L.

The medical stapler anvil 100 includes a composite moment of inertia including the anvil pocket beam moment of inertia and the anvil back beam moment of inertia and lying in a range of approximately 0.000015 to approximately 0.000035 in$^4$. In some examples, the composite moment of inertia can be approximately 0.000025 in$^4$. As discussed herein, unless otherwise specifically stated, moments of inertia refers to bending moments of inertia (also sometimes called second moments of area) and are evaluated with the longitudinal axis L-L as the principal axis. In plain terms, the moments of inertia of referred to throughout this disclosure affect how apt a component is to bend when subjected to a clamping load applied by the stapler 200, such as on tissue, as discussed in relation to FIG. 1. In some examples, first section 110 and second section 130 have approximately equal moments of inertia with respect to the longitudinal axis L-L.

Anvil pocket beam 130 can further an anvil pocket beam stiffness, and, likewise, the anvil back beam 110 can further include an anvil back beam stiffness approximately equal to the anvil pocket beam stiffness. Importantly, this allows both components (back beam 110 and pocket beam 130), when interconnected such as by welding as described herein, to contribute equally significant portions of the stiffness and clamping pressure exerted on the anvil.

The anvil back beam 110 is formed from a shaped sheet. In some examples, the anvil back beam 110 and the anvil pocket beam 130 are each formed from one or more sheets of metal having equal thicknesses. Generally, as seen in the cross-sections shown in FIG. 2B-3B and FIG. 4A-4B, the crown 112 can include a central ridge 114 parallel to the longitudinal axis L-L and two lateral sides 114a, 114b extending therefrom. In FIG. 2B-3B, central ridge 114 is curved more tightly than the flatter central ridge 114 shown in FIGS. 4A-4B.

As shown in FIGS. 2A-3B, each lateral side 114a, 114b can include a curled end 122a, 122b, an outer edge 120a, 120b disposed proximate the respective folded edge 134a, 134b, an inferior ridge 116a, 116b, and a trough 118a, 118b disposed between the inferior ridge 116a, 116b and the central ridge 114. As used herein, the term "curled" is to be understood as embodied by its ordinary meaning in the art of sheet metal working while being inclusive of other sheet metal geometries which can have other technical names but still mean generally that an end of a metal sheet is made to turn back toward said metal sheet. That is to say, the term "curled" is inclusive of sheet metal geometries including the following non-exhaustive list: on-center curls, off-center curls, hems, rope hems, teardrop hems, rolled hems, closed hems, open hems, and beads. In some examples, each curled end 122a, 122b terminates proximate an axis AIR of the respective inferior ridge 116a, 116b. In other words, the first curled end 122a at least partially intersects an axis AIR of the first inferior ridge 116a, and the second curled end 122b at least partially intersects axis AIR of the second inferior ridge 116b.

Figure 2B:
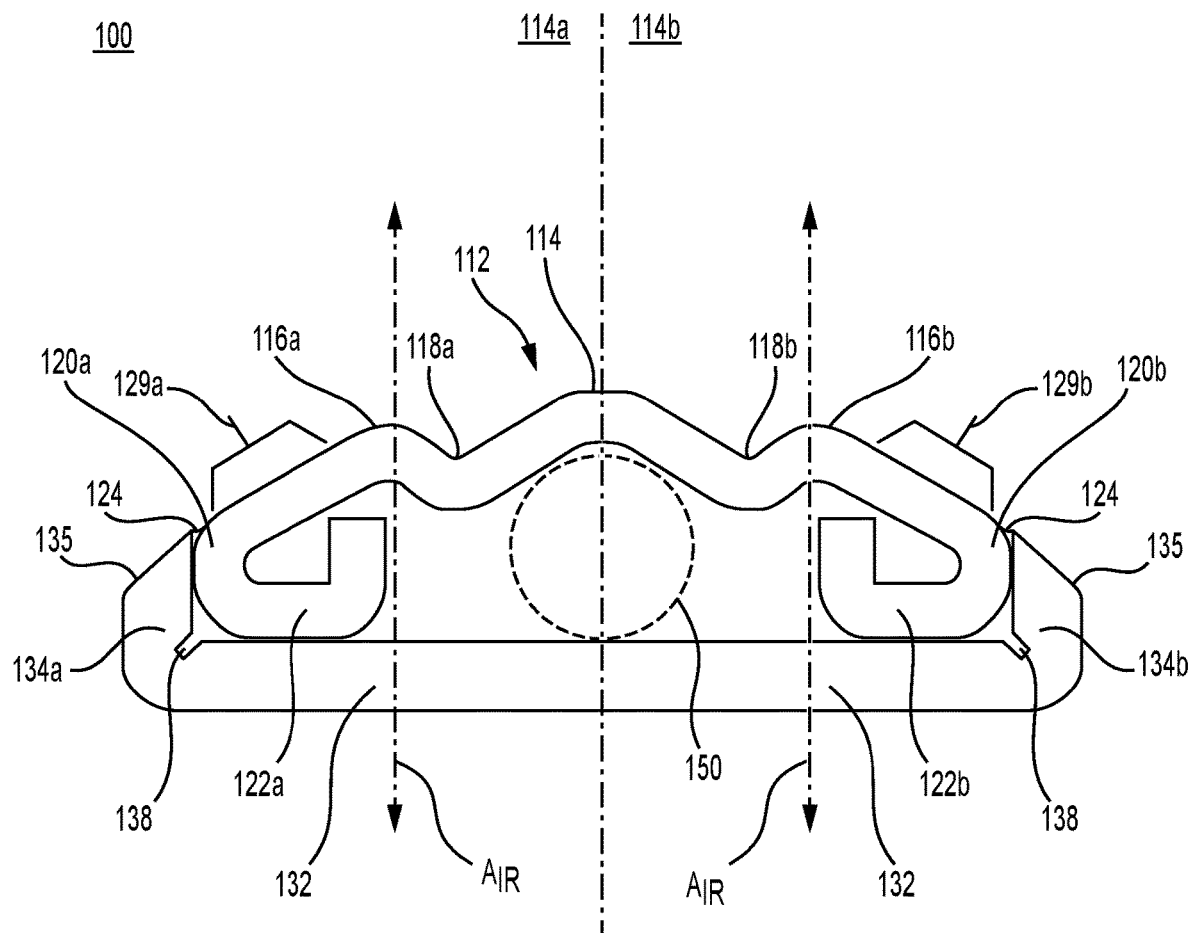
FIG. 2B shows a distal end cross-section of the medical stapler anvil of FIG. 1, according to aspects of the present disclosure.

As shown in FIG. 2B, the anvil pocket beam 130 includes a pocket surface 132 in contact with anvil back beam 110 and two folded edges 134. The two folded edges 134 can each include a sloped end 135 such that the sloped ends 135 are generally coplanar with a respective portion 129a, 129b of the sheet extending between the inferior ridge 116a, 116b and the outer edge 120a, 120b. That is to say, there is a smooth transition from the two folded edges 134 to the anvil pocket beam 130. Phrased otherwise, the first folded edge 134a and the second folded edge 134b can be chamfered or beveled so as to form ends 135a, 135b which alone or in combination with welds 124, create a smooth outer profile of anvil 100 proximate said welds 124. In addition to welds 124, the anvil pocket beam 130 and the anvil back beam 110 can interface at contact areas between curled ends 122a, 122b and both the folded edges 134a, 134b and the pocket surface 132.

Stated otherwise, the stamped sheet metal anvil 100 for medical stapler 200 extends along a longitudinal axis L-L from a proximal end 102 to a distal end 104 and includes a first section 110 and a second section 130. The first section 110 includes a shaped sheet 112 with a central ridge 114 formed therein such that the central ridge 114 is parallel to the longitudinal axis L-L, a first lateral side 114a extending from the central ridge 114, and a second lateral side 114b extending from the central ridge opposite the first 114a. Generally, the central ridge 114 can be considered to lie in a plane perpendicular to the anvil pocket beam 130. The first lateral side 114a can include a first inferior ridge 116a, a first trough 118a disposed between the first inferior ridge 116a and the central ridge 114, a first outer edge 120a, and a first curled end 122a. Similarly, the second lateral side 114b can include a second inferior ridge 116b, a second trough 118b disposed between the second inferior ridge 116b and the central ridge 114, a second outer edge 120b, and a second curled end 122b.

The second section 130 can include a pocket surface 132 in contact with the first and second curled ends 122a, 122b, a first folded edge 134a disposed proximate the first outer edge 120a, and a second folded edge 134b disposed proximate the second outer edge 120b.

In part to achieve the attachment of the anvil pocket beam 130 to the anvil back beam 110, each lateral side 114a, 114b can include a weld 124 joining the outer edge 120a, 120b to the respective folded edges 134 of the anvil pocket beam 130. The two folded edges 134 and their respective sloped end 135 can be shaped or sized specifically to accommodate welds 124 while still maintaining the smooth transition from the two folded edges 134 to the anvil pocket beam 130.

Figure 3A:
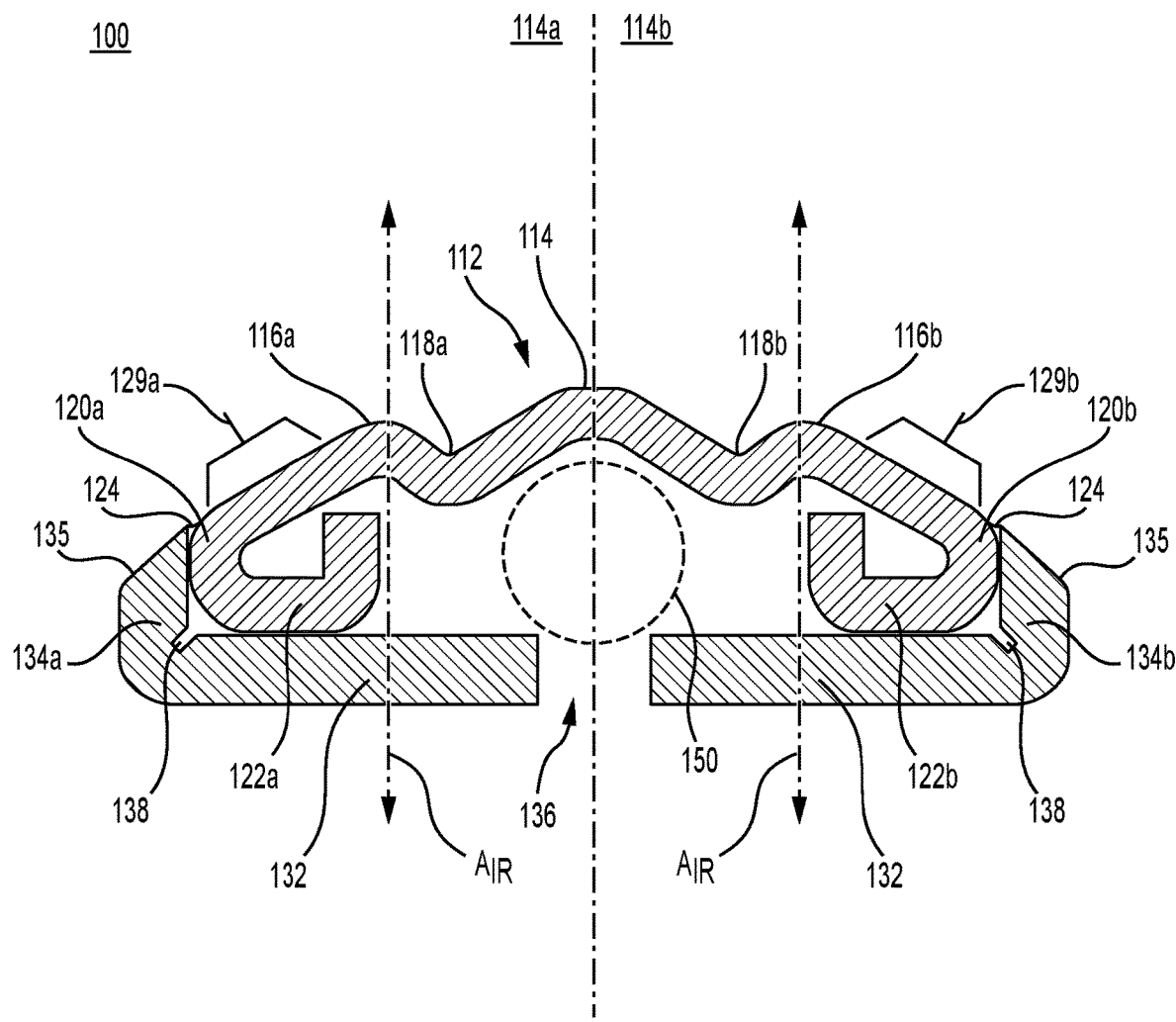
FIG. 3A shows a cross-section of an anvil for a medical stapler along line 3-3 of FIG. 2A, according to aspects of the present disclosure.
Figure 3B:
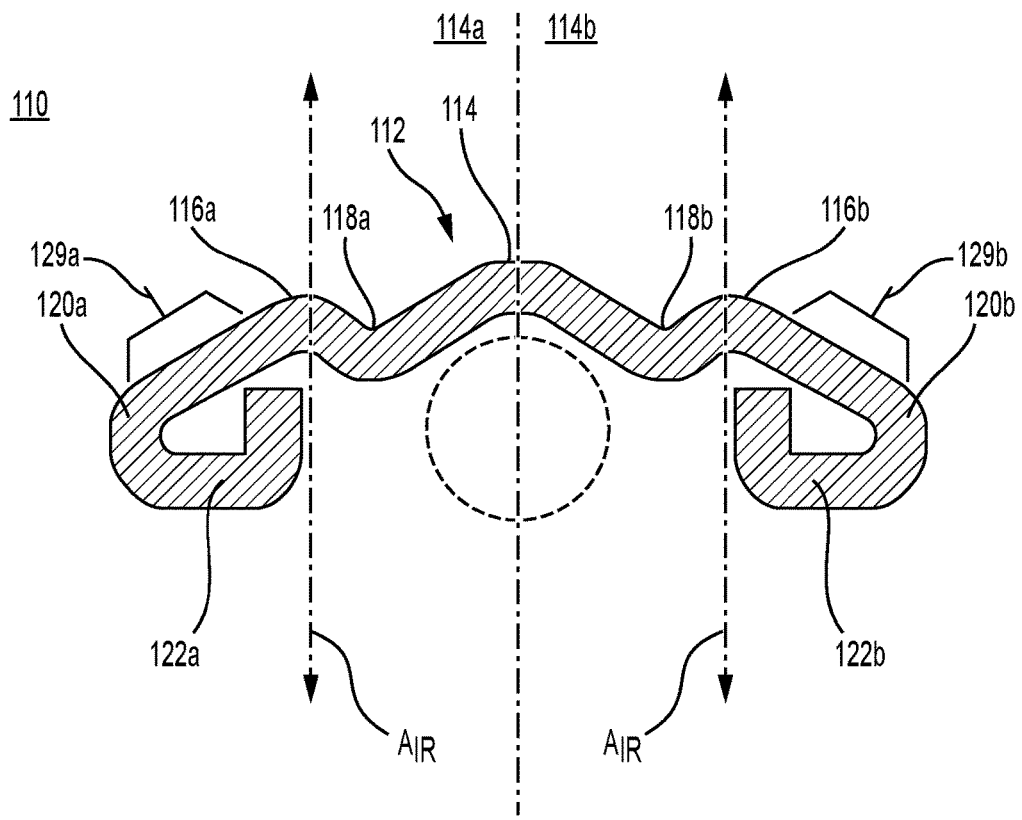
FIG. 3B shows a cross-section of an anvil back beam, according to aspects of the present disclosure.
Figure 3C:
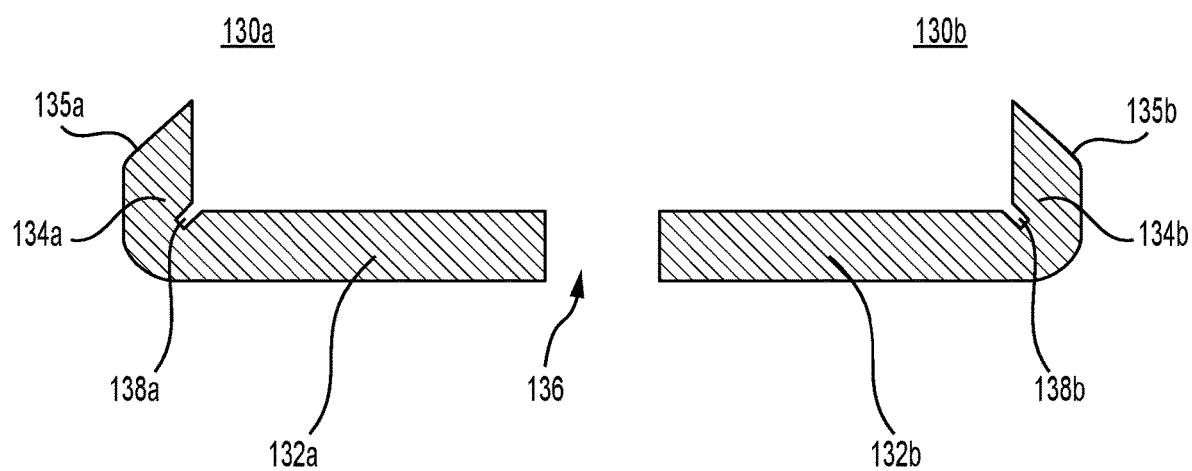
FIG. 3C shows a cross-section of an anvil pocket beam, according to aspects of the present disclosure.

As seen in FIG. 3A and FIG. 3C, the anvil pocket beam 130 can further include a slot 136 extending parallel to the longitudinal axis L-L and formed in the pocket surface 132. It should be noted that slot 136 does not necessarily extend the entire length of the anvil pocket beam and indeed the slot 136 may terminate proximate, but before reaching, the proximal end 102 and the distal end 104, respectively. As such, a cross-section taken approximately at the halfway point between the proximal end 102 and the distal end 104 can resemble that shown in FIG. 3A while a cross-section taken proximate the proximal end 102 or the distal end 104 resembles that shown in FIG. 2B.

Alternatively, the anvil pocket beam 130 can further include a first beam 130a including approximately half of the plurality of staple forming pockets 142 and a second beam 130b comprising a remainder of the plurality of staple forming pockets 142. The first 130a and second 130b beams can be fixedly attached to opposite lateral portions 123a, 123b of the anvil back beam along a longitudinal axis L-L. This results in a slot 136 being formed between the first 130a and second 130b beams and extending parallel to the longitudinal axis L-L.

Furthermore, as shown in FIGS. 2B-3B, a channel 150 can be formed between the anvil pocket beam 130 and the anvil back beam 110, formed partially between the crown 112 and the slot 136, and in partial communication with the slot 136.

In some examples, the central ridge 114, the troughs 118a, 118b, and the pocket surface 132 form channel 150, and channel 150 is configured to constrain a knife member (not shown) of medical stapler 200.

In any of these examples, channel 150 can be a longitudinally extending upper knife channel through which a knife member can translate thus severing stapled tissue clamped between the staple cartridge jaw and the anvil jaw. Though channel 150 is depicted in the cross-sections as a dotted circle, it should be understood that the channel 150 can be any generally longitudinal space defined by the inner bounds of the anvil back beam 110 and the anvil pocket beam 130, and further that the knife member can include protrusions which serve to constrain the knife member within the channel 150. It should be understood that the part of the knife member which translates through channel 150 can be shaped according to the geometry of the anvil 100 so that it rides smoothly through the channel 150 without binding.

The anvil pocket beam 130 can include relief cuts 138 between the pocket surface 132 and the folded edges 134. Said relief cuts 138 can be provided so that the edges 134 can be more easily and precisely folded from a flat sheet during the manufacturing process. Additionally, relief cuts 138 can be angled more toward the pocket surface 132 than the folded edges 134 in order to increase the moment of inertia of the pocket beam 130 and/or to make the pocket beam moment of inertia more equal to the anvil back beam moment of inertia. Furthermore, the relief cuts 138 can be made deeper or shallower to further tune the pocket beam moment of inertia.

Figure 4A:
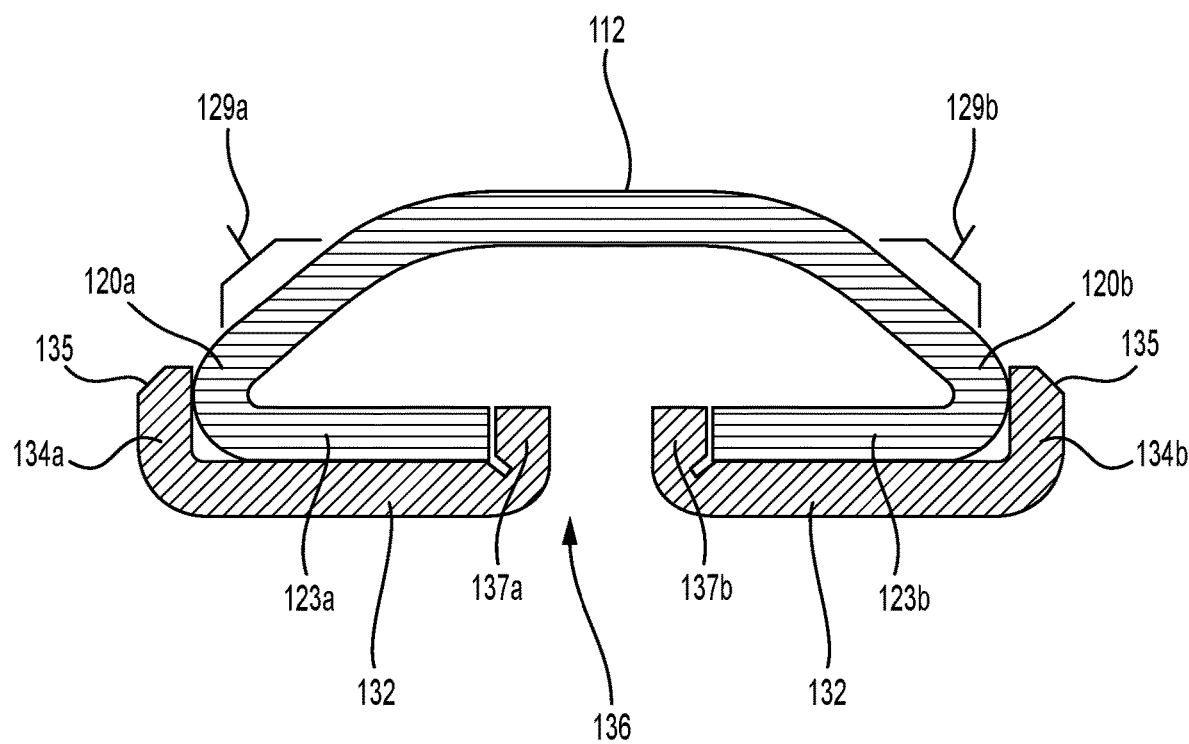
FIG. 4A shows a cross-section of another example of an anvil for a medical stapler, according to aspects of the present disclosure.
Figure 4B:
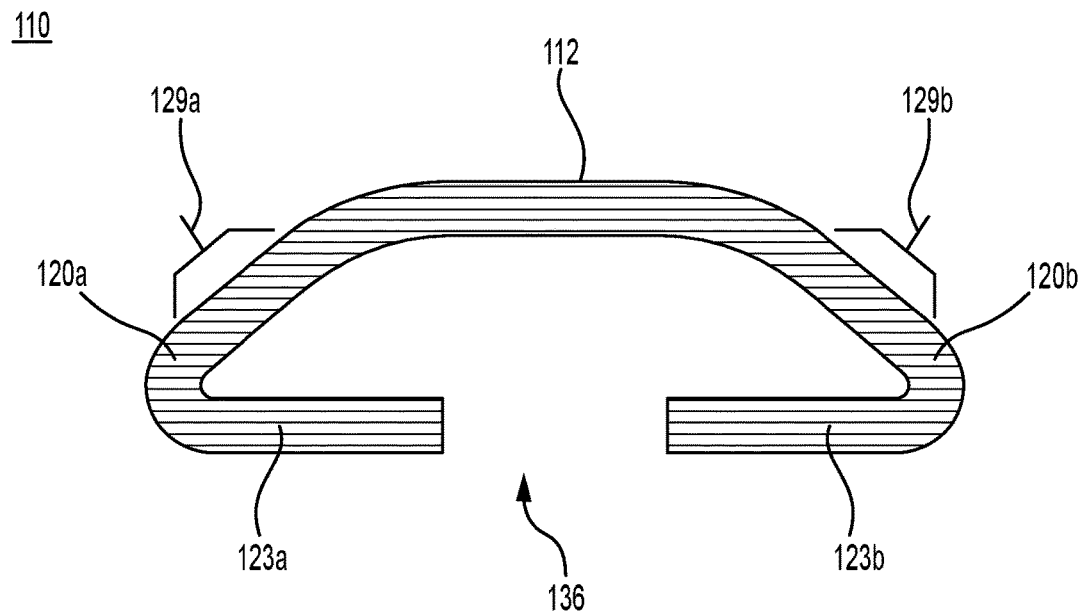
FIG. 4B shows a cross-section of the other example of FIG. 4A of an anvil back beam, according to aspects of the present disclosure.
Figure 4C:
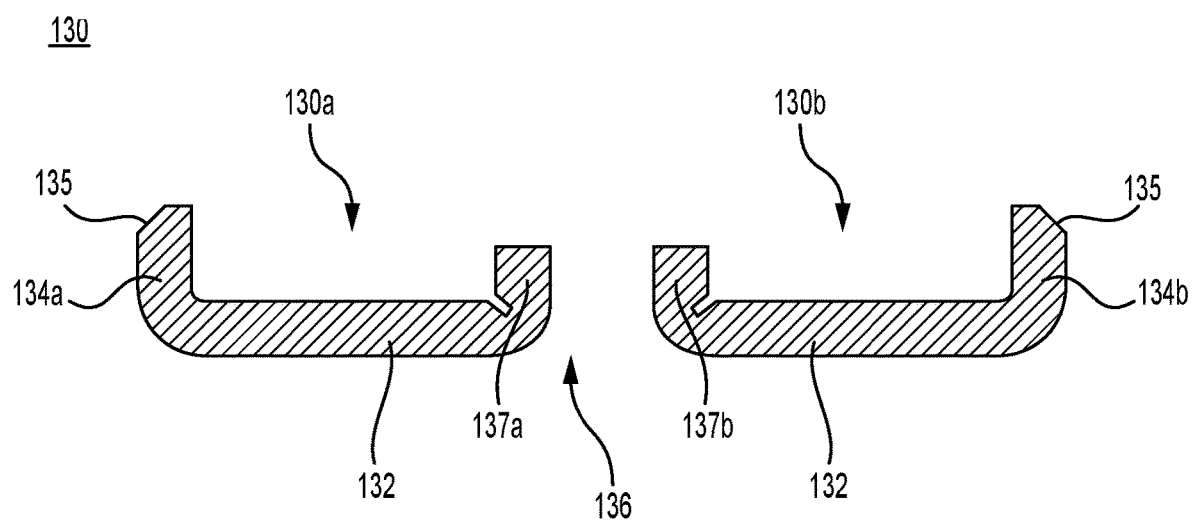
FIG. 4C shows a cross-section of the other example of FIG. 4A of an anvil pocket beam, according to aspects of the present disclosure.

Another example of the medical stapler anvil 100 is shown in FIG. 4A. As mentioned previously, the anvil back beam 110 of the anvil 100 of FIG. 4A has a wider central ridge 114 and no inferior ridges. FIG. 4B depicts only the anvil back beam 110 of the anvil of FIG. 4A, and FIG. 4C depicts only the pocket beam 130 of the anvil of FIG. 4A.

Figure 5C:
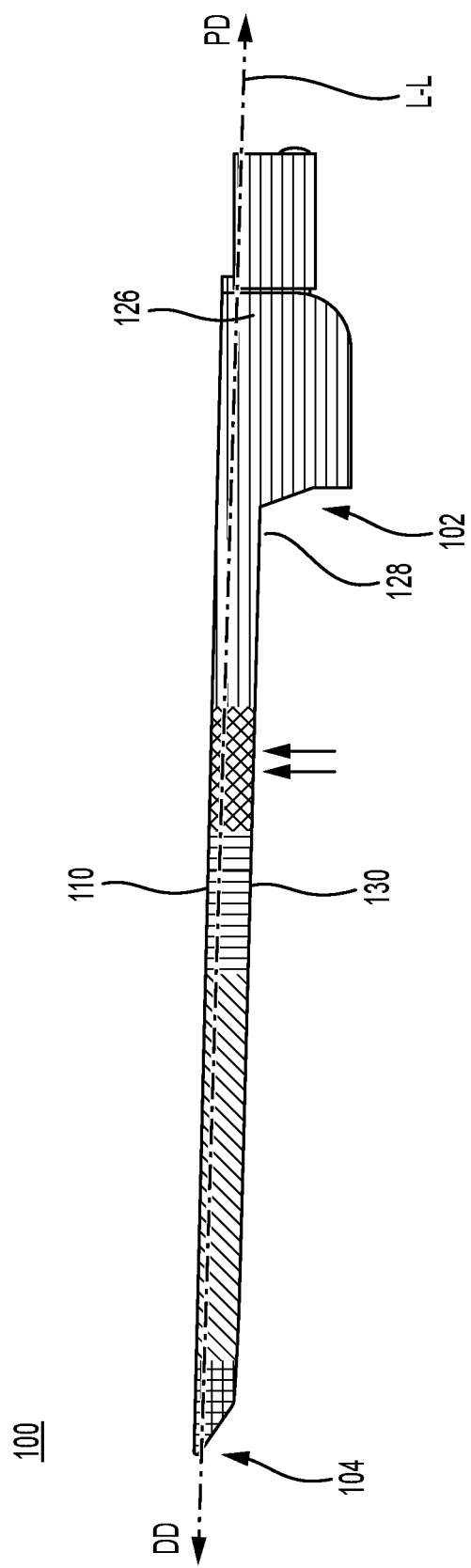
FIG. 5C shows a side view of a medical stapler anvil, according to aspects of the present disclosure.

FIGS. 5A-5C show side profiles of the medical stapler anvil 100. Though the coupling portion 126 in the example shown in FIG. 5A is formed form simply downfolding two portion of an initially flat sheet, anvil 100 can further include a weld 128 joining the coupling portion 126 to the second section 130 as can be seen FIGS. 5B-5C. This weld 128 can reduce the stress concentration at the transition between coupling portion 126 and the back beam 110 and pocket beam 130 of the anvil.

Figures 6A, 6B:
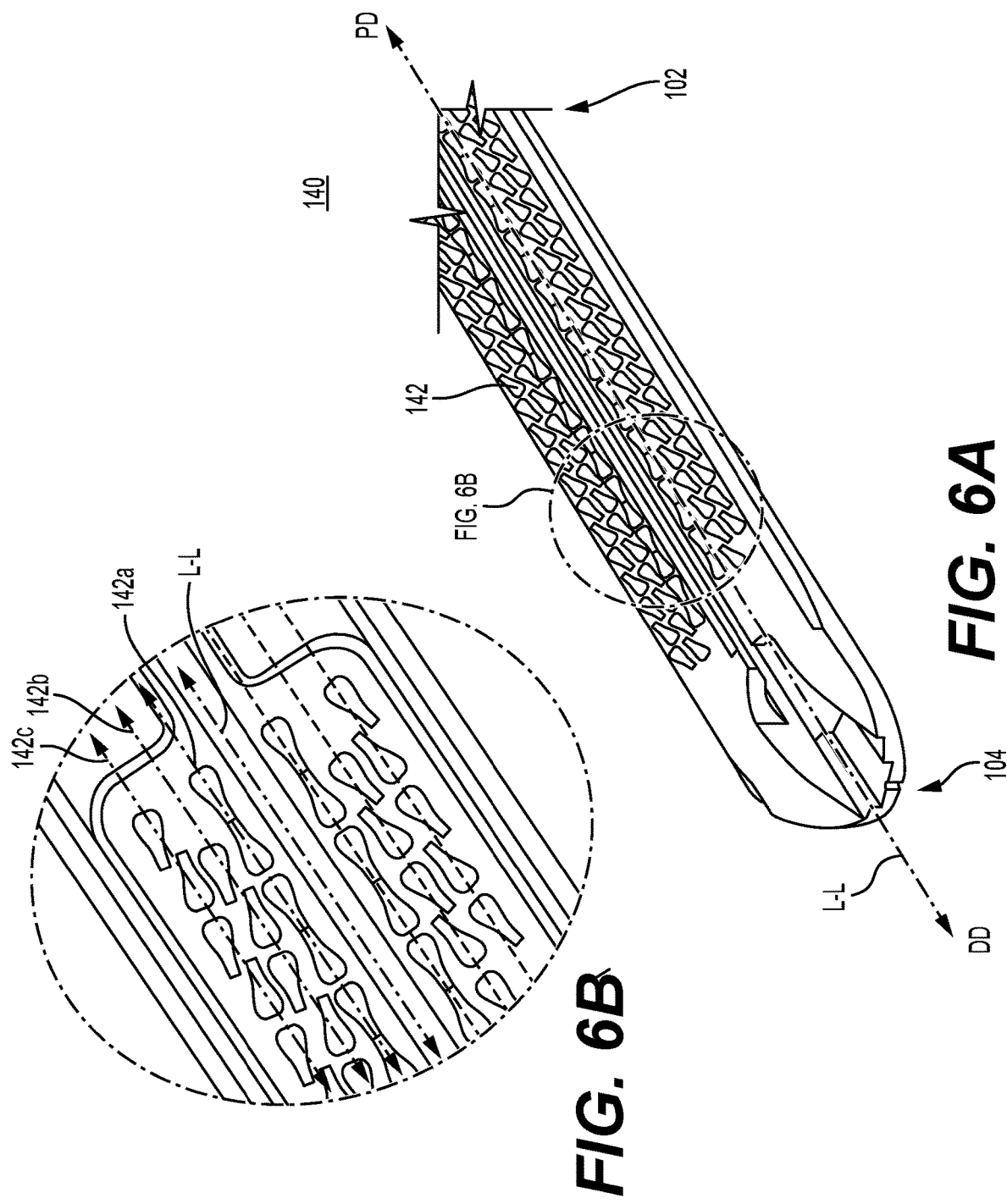
FIG. 6A shows a perspective view of an anvil for a medical stapler, according to aspects of the present disclosure.
FIG. 6B shows a detail view of the staple forming pockets on the anvil in FIG. 6A, according to aspects of the present disclosure.

As shown in FIG. 6A-6B, the pocket surface 132 can include the plurality of staple forming pockets 142d, which can be stamped, machined, or otherwise formed therein. The plurality of staple forming pockets 142 can be arranged in a first column 142a parallel to the longitudinal axis L-L and a second column 142b at least partially aligned obliquely to the longitudinal axis L-L. Some examples include a third column 142c with at least some of the staple forming pockets 142d aligned obliquely to the longitudinal axis L-L.

Figure 7:
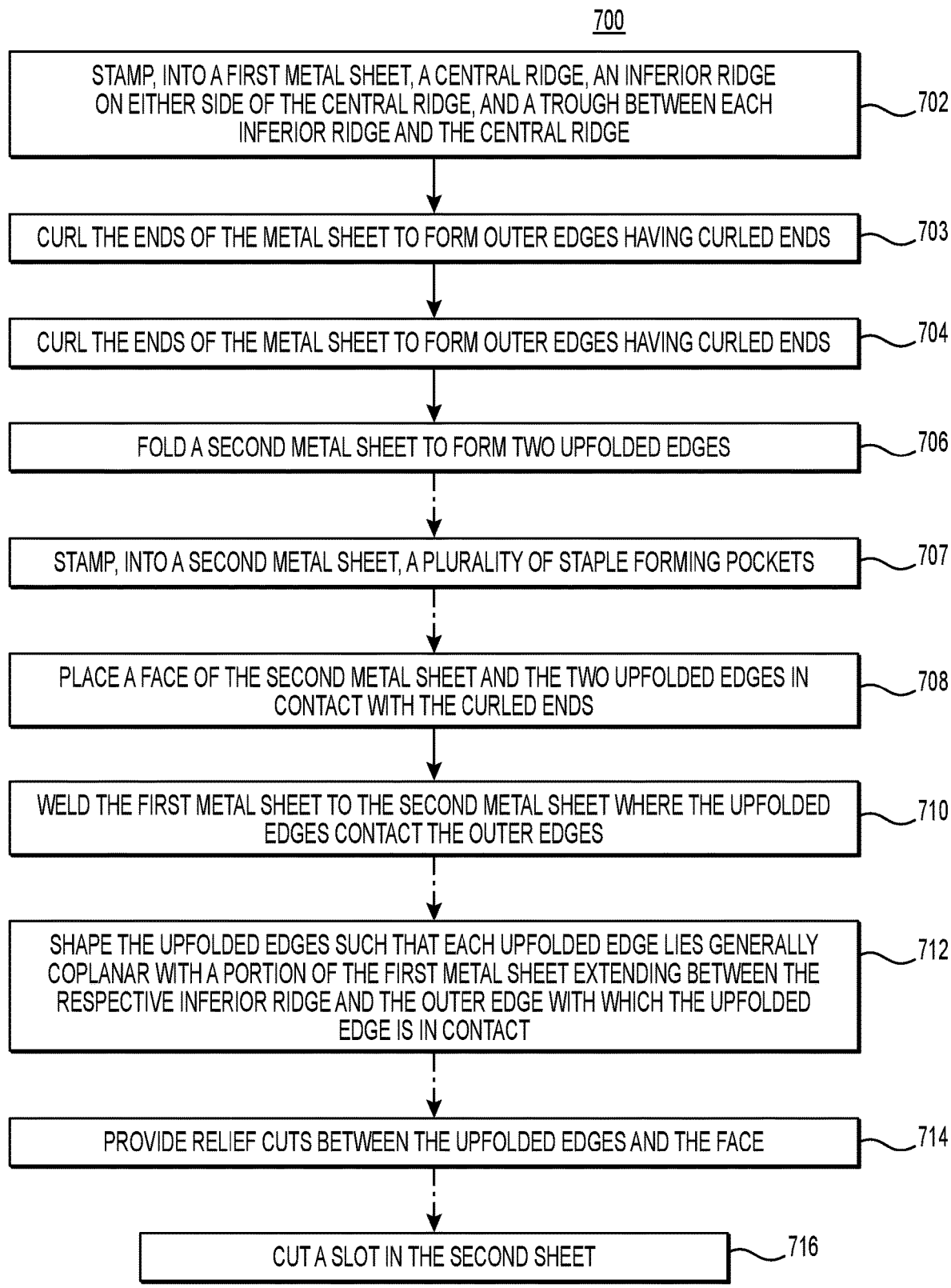
FIG. 7 provides a flowchart of a method of, according to aspects of the present disclosure.

FIG. 7 shows a method 700 of forming an anvil for use in a medical stapler. Method 700 can in some examples form anvil 100 as detailed above, with all of its components, subcomponents, and features.

Method 700 can include stamping 702 a central ridge into a first metal sheet, curling 704 ends of the first metal sheet to form outer edges having curled ends, folding 706 a second metal sheet to form two upfolded edges, stamping 707 a plurality of staple forming pockets into the second metal sheet, placing 708 a pocket surface of the second metal sheet and the two upfolded edges in contact with the curled ends, and welding 710 the first metal sheet to the second metal sheet where the upfolded edges contact the outer edges.

Method 700 can also include stamping 703, into the first metal sheet, an inferior ridge on either side of the central ridge, and a trough between each inferior ridge and the central ridge. This stamping 703 can for example result in the forming in the first metal sheet of the inferior ridges 116a, 116b.

Method 700 can further include shaping 712 the upfolded edges such that each upfolded edge lies generally coplanar with a portion of the first metal sheet extending between the respective inferior ridge and the outer edge with which the upfolded edge is in contact. This results in a smooth transition between the upfolded edges and the first metal sheet, especially if the shaping 712 accounts for the welding step 710, and an example of this resulting union is depicted in FIG. 3A and described herein in relation thereto.

Method 700 can further include providing 714 relief cuts between the upfolded edges and the pocket surface. Method 700 can also further include cutting 716 a slot in the second sheet.

In some examples, stamping 707 the plurality of staple forming pockets into the second metal sheet comprises stamping a first column of staple forming pockets aligned parallel to a longitudinal axis L-L of the anvil and a second column of staple forming pockets, at least a portion of the staple forming pockets of the second column of staple forming pockets aligned oblique to the longitudinal axis L-L.

As used herein, the term stamping includes broadly those methods for forming sheets of material, namely metal, by using pressure, and these include bending, flanging, embossing, blanking, coining, drawing, stretching, ironing, necking, curling, hemming, piercing, forced extrusion, and cutting. These methods can be used in combination with other fabrication methods such as those mentioned herein and further including machining and additive manufacturing.

It should be appreciated that the method 700 just described can include more or fewer steps or features than those described. Furthermore, the steps or features can be performed in different orders and should not be construed as being required to be performed in any particular order.

Figure 8:
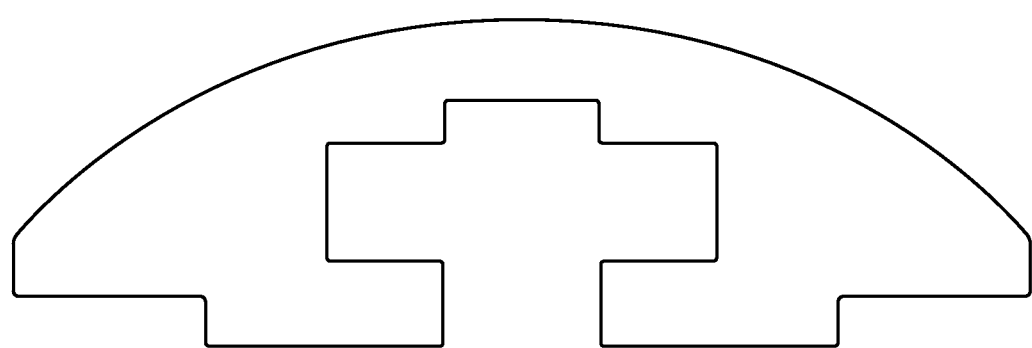
FIG. 8 shows a cross-section of a medical stapler anvil, according to aspects of the prior art.

FIG. 8 shows a cross-section of a prior art medical stapler anvil. It should be noted that it is machined from a single solid billet.

The disclosed technology described herein can be further understood according to the following clauses:

Clause 1: A medical stapler anvil comprising: an anvil pocket beam comprising: a plurality of staple forming pockets; and an anvil pocket beam moment of inertia; an anvil back beam fixedly attached to the anvil pocket beam, comprising: a crown disposed opposite the plurality of staple forming pockets; and an anvil back beam moment of inertia approximately equal to the anvil pocket beam moment of inertia.

Clause 2: The medical stapler anvil of clause 1, the anvil pocket beam further comprising an anvil pocket beam stiffness; and the anvil back beam further comprising an anvil back beam stiffness approximately equal to the anvil pocket beam stiffness.

Clause 3: The medical stapler anvil of clauses 1 or 2, further comprising: a composite moment of inertia comprising the anvil pocket beam moment of inertia and the anvil back beam moment of inertia and comprising a range of 0.000015 to approximately 0.000035 in$^4$.

Clause 4: The medical stapler anvil of any of clauses 1-3 further comprising: a proximal end; a distal end; and a longitudinal axis between the proximal and distal ends, wherein the anvil back beam is formed from a shaped sheet, wherein the crown comprises: a central ridge parallel to the longitudinal axis; and two lateral sides extending therefrom, and wherein the anvil pocket beam further comprises: a pocket surface in contact with anvil back beam; and two folded edges.

Clause 5: The medical stapler anvil of clause 4, each lateral side comprising: a curled end; an outer edge disposed proximate the respective folded edge; an inferior ridge; and a trough disposed between the inferior ridge and the central ridge.

Clause 6: The medical stapler anvil of clause 5, each curled end terminating proximate an axis of the respective inferior ridge.

Clause 7: The medical stapler anvil of any of clauses 4-6, the two folded edges each comprising a sloped end such that the sloped ends are generally coplanar with a respective portion of the sheet extending between the inferior ridge and the outer edge.

Clause 8: The medical stapler anvil of any of clauses 4-7, the anvil pocket beam further comprising relief cuts between the pocket surface and the folded edges.

Clause 9: The medical stapler anvil of any of clauses 4-8, each lateral side comprising a weld joining the outer edge to the respective folded edges of the anvil pocket beam.

Clause 10: The medical stapler anvil of any of clauses 1-9, the anvil pocket beam further comprising: a slot extending parallel to the longitudinal axis and formed in the pocket surface, and wherein the pocket surface comprises the plurality of staple forming pockets.

Clause 11: The medical stapler anvil of clause 1, wherein the anvil pocket beam further comprises: a first beam comprising approximately half of the plurality of staple forming pockets; and a second beam comprising a remainder of the plurality of staple forming pockets; the first and second beams fixedly attached to opposite lateral portions of the anvil back beam along a longitudinal axis; and a slot formed between the first and second beams and extending parallel to the longitudinal axis.

Clause 12: The medical stapler anvil of any of clauses 1-11, further comprising: a channel formed between the anvil pocket beam and the anvil back beam, formed partially between the crown and the slot, and in partial communication with the slot.

Clause 13: The medical stapler anvil of any of clauses 1-12, the anvil further comprising a coupling portion disposed proximate the proximal end of the anvil.

Clause 14: The medical stapler anvil of any of clauses 1-13, wherein the central ridge, the troughs, and the pocket surface form a channel configured to constrain a knife member of a medical stapler.

Clause 15: The medical stapler anvil of any of clauses 1-14, wherein the anvil back beam and the anvil pocket beam are each formed from one or more sheets of metal having equal thicknesses.

Clause 16: An anvil for a medical stapler, the anvil extending along a longitudinal axis from a proximal end to a distal end and comprising: a first section comprising: a shaped sheet comprising: a central ridge parallel to the longitudinal axis; a first lateral side extending from the central ridge and comprising; a first inferior ridge; a first trough disposed between the first inferior ridge and the central ridge; a first outer edge; and a first curled end; a second lateral side extending from the central ridge and comprising; a second inferior ridge; a second trough disposed between the second inferior ridge and the central ridge; a second outer edge; and a second curled end; and a second section comprising: a pocket surface in contact with the first and second curled ends; a first folded edge disposed proximate the first outer edge; and a second folded edge disposed proximate the second outer edge.

Clause 17: The anvil of clause 16, wherein the first and second curled ends terminating proximate an axis of the respective first and second inferior ridge.

Clause 18: The anvil of clause 17, the first and second folded edges each comprising a respective sloped end generally coplanar with a respective first and second portions of the shaped sheet extending between the first and second inferior ridges and the first and second outer edges, respectively.

Clause 19: The anvil of clause 18, the second section further comprising relief cuts between the pocket surface the folded edges.

Clause 20: The anvil of clause 19, each of the first and second lateral sides of the first section comprising a weld joining the outer edge to the respective folded edges of the second section.

Clause 21: The anvil of clause 20, wherein the pocket surface of the second section is flat.

Clause 22: The anvil of clause 21, the pocket surface comprising a slot extending parallel to the longitudinal axis.

Clause 23: The anvil of clause 22, further comprising a plurality of staple forming pockets disposed proximate the pocket surface and configured to curl a plurality of staples projected against the plurality of staple forming pockets.

Clause 24: The anvil of clause 24, the shaped sheet further comprising a coupling portion disposed proximate the proximal end of the anvil.

Clause 25: The anvil of clause 24, further comprising a weld joining the coupling portion to the second section.

Clause 26: The anvil of clause 25, wherein the first section and the second section have approximately equal moments of inertia with respect to the longitudinal axis.

Clause 27: The anvil of clause 26, wherein the central ridge, the inferior ridges, and the pocket surface form a channel configured to constrain a knife member of a medical stapler.

Clause 28: The anvil of clause 27, wherein the first section and the second section are each formed from one or more metal sheets having equal thicknesses.

Clause 29: The anvil of clause 28, the plurality of staple forming pockets comprising: a first column of staple forming pockets aligned parallel to the longitudinal axis; and a second column of staple forming pockets, at least a portion of the staple forming pockets of the second column of staple forming pockets aligned oblique to the longitudinal axis.

Clause 30: The anvil of clause 29, the plurality of staple forming pockets further comprising: a third column of staple forming pockets, at least a portion of the staple forming pockets of the third column of staple forming pockets aligned oblique to the longitudinal axis.

Clause 31: A method of forming an anvil for use in a medical stapler, the method comprising: stamping, into a first metal sheet, a central ridge; curling ends of the first metal sheet to form outer edges having curled ends; folding a second metal sheet to form two upfolded edges; stamping, into the second metal sheet, a plurality of staple forming pockets; placing a pocket surface of the second metal sheet and the two upfolded edges in contact with the curled ends; and welding the first metal sheet to the second metal sheet where the upfolded edges contact the outer edges.

Clause 32: The method of clause 31, further comprising: stamping, into the first metal sheet, an inferior ridge on either side of the central ridge, and a trough between each inferior ridge and the central ridge.

Clause 33: The method of clause 31, further comprising: shaping the upfolded edges such that each upfolded edge lies generally coplanar with a portion of the first metal sheet extending between the respective inferior ridge and the outer edge with which the upfolded edge is in contact.

Clause 34: The method of clause 33, further comprising: providing relief cuts between the upfolded edges and the pocket surface.

Clause 35: The method of clause 34, further comprising: cutting a slot in the second sheet.

Clause 36: The method of clause 31, wherein stamping the plurality of staple forming pockets into the second metal sheet comprises stamping a first column of staple forming pockets aligned parallel to a longitudinal axis of the anvil and a second column of staple forming pockets, at least a portion of the staple forming pockets of the second column of staple forming pockets aligned oblique to the longitudinal axis.

The embodiments described above are cited by way of example, and the present invention is not limited by what has been particularly shown and described hereinabove. Rather, the scope of the invention includes both combinations and sub combinations of the various features described and illustrated hereinabove, as well as variations and modifications thereof which would occur to persons skilled in the art upon reading the foregoing description and which are not disclosed in the prior art.

The invention claimed is:

1. A medical stapler anvil comprising:
an anvil pocket beam with an anvil pocket beam stiffness, the anvil pocket beam comprising:
an anvil pocket beam stiffness;
a plurality of staple forming pockets; and
an anvil pocket beam moment of inertia;
an anvil back beam fixedly attached to the anvil pocket beam, comprising:
an anvil back beam stiffness approximately equal to the anvil pocket beam stiffness;
a crown disposed opposite the plurality of staple forming pockets; and
an anvil back beam moment of inertia approximately equal to the anvil pocket beam moment of inertia; and
a composite moment of inertia comprising the anvil pocket beam moment of inertia and the anvil back beam moment of inertia and comprising a range of 0.000015 to approximately 0.000035 $in^4$.

2. A medical stapler anvil comprising:
an anvil pocket beam having an anvil pocket beam stiffness, the anvil pocket beam further comprising:
a plurality of staple forming pockets; and
an anvil pocket beam moment of inertia;
an anvil back beam fixedly attached to the anvil pocket beam comprising:
an anvil back beam stiffness approximately equal to the anvil pocket beam stiffness;
a crown disposed opposite the plurality of staple forming pockets; and
an anvil back beam moment of inertia approximately equal to the anvil pocket beam moment of inertia;
a proximal end;
a distal end; and
a longitudinal axis between the proximal and distal ends, wherein the anvil back beam is formed from a shaped sheet, wherein the crown comprises:
a central ridge parallel to the longitudinal axis; and
two lateral sides extending therefrom, and wherein the anvil pocket beam further comprises a pocket surface in contact with anvil back beam, and two folded edges.

3. The medical stapler anvil of claim 2, each lateral side comprising:
a curled end;
an outer edge disposed proximate the respective folded edge;
an inferior ridge; and
a trough disposed between the inferior ridge and the central ridge.

4. The medical stapler anvil of claim 3, each curled end terminating proximate an axis of the respective inferior ridge.

5. The medical stapler anvil of claim 4, the two folded edges each comprising a sloped end such that the sloped ends are generally coplanar with a respective portion of the sheet extending between the inferior ridge and the outer edge.

6. The medical stapler anvil of claim 5, the anvil pocket beam further comprising relief cuts between the pocket surface and the folded edges.

7. The medical stapler anvil of claim 6, each lateral side comprising a weld joining the outer edge to the respective folded edges of the anvil pocket beam.

8. The medical stapler anvil of claim 7, the anvil pocket beam further comprising: a slot extending parallel to the longitudinal axis and formed in the pocket surface, and wherein the pocket surface comprises the plurality of staple forming pockets.

9. A medical stapler anvil comprising:
an anvil pocket beam comprising:
a plurality of staple forming pockets; and
an anvil pocket beam moment of inertia;
a first beam comprising approximately half of the plurality of staple forming pockets; and
a second beam comprising a remainder of the plurality of staple forming pockets; and
a slot formed between the first and second beams and extending parallel to a longitudinal axis;
an anvil back beam fixedly attached to the anvil pocket beam, comprising:
a crown disposed opposite the plurality of staple forming pockets; and
an anvil back beam moment of inertia approximately equal to the anvil pocket beam moment of inertia,
wherein the first and second beams fixedly attached to opposite lateral portions of the anvil back beam along the longitudinal axis, wherein the anvil back beam and the anvil pocket beam are each formed from one or more sheets of metal having equal thicknesses.

10. The medical stapler anvil of claim 9, further comprising:

a channel formed between the anvil pocket beam and the anvil back beam, formed partially between the crown and the slot, and in partial communication with the slot.

11. The medical stapler anvil of claim 10, the anvil further comprising a coupling portion disposed proximate a proximal end of the anvil.

12. An anvil for a medical stapler, the anvil extending along a longitudinal axis from a proximal end to a distal end and comprising:

a first section comprising:
  a shaped sheet comprising:
    a central ridge parallel to the longitudinal axis;
    a first lateral side extending from the central ridge and comprising;
      a first inferior ridge;
      a first trough disposed between the first inferior ridge and the central ridge;
      a first outer edge; and
      a first curled end;
    a second lateral side extending from the central ridge and comprising;
      a second inferior ridge;
      a second trough disposed between the second inferior ridge and the central ridge;
      a second outer edge; and
      a second curled end; and
  a second section comprising:
    a pocket surface in contact with the first and second curled ends;
    a first folded edge disposed proximate the first outer edge; and
    a second folded edge disposed proximate the second outer edge.

13. The anvil of claim 12, wherein the first and second curled ends terminating proximate an axis of the respective first and second inferior ridge.

14. The anvil of claim 13, the first and second folded edges each comprising a respective sloped end generally coplanar with a respective first and second portions of the shaped sheet extending between the first and second inferior ridges and the first and second outer edges, respectively.

15. The anvil of claim 14, the second section further comprising relief cuts between the pocket surface the folded edges.

16. The anvil of claim 15, each of the first and second lateral sides of the first section comprising a weld joining the outer edge to the respective folded edges of the second section.

* * * * *